US 11,365,214 B2

(12) United States Patent
Zhang et al.

(10) Patent No.: US 11,365,214 B2
(45) Date of Patent: Jun. 21, 2022

(54) METHOD FOR PRETREATING PROTEIN IN EX VIVO BODY FLUID

(71) Applicant: DALIAN INSTITUTE OF CHEMICAL PHYSICS, CHINESE ACADEMY OF SCIENCES, Liaoning (CN)

(72) Inventors: Lihua Zhang, Liaoning (CN); Huiming Yuan, Liaoning (CN); Zhigang Sui, Liaoning (CN); Kaiguang Yang, Liaoning (CN); Yukui Zhang, Liaoning (CN)

(73) Assignee: DALIAN INSTITUTE OF CHEMICAL PHYSICS, CHINESE ACADEMY OF SCIENCES, Liaoning (CN)

( * ) Notice: Subject to any disclaimer, the term of this patent is extended or adjusted under 35 U.S.C. 154(b) by 687 days.

(21) Appl. No.: 16/462,464
(22) PCT Filed: Jul. 12, 2017
(86) PCT No.: PCT/CN2017/092553
§ 371 (c)(1),
(2) Date: May 20, 2019
(87) PCT Pub. No.: WO2018/090651
PCT Pub. Date: May 24, 2018

(65) Prior Publication Data
US 2019/0375784 A1    Dec. 12, 2019

(30) Foreign Application Priority Data
Nov. 21, 2016  (CN) .......................... 201611043619.6

(51) Int. Cl.
C07K 1/14    (2006.01)
C12Q 1/37    (2006.01)
(Continued)

(52) U.S. Cl.
CPC ................ C07K 1/145 (2013.01); C12Q 1/37 (2013.01); G01N 1/4044 (2013.01);
(Continued)

(58) Field of Classification Search
CPC ........ C07K 1/145; C12Q 1/37; G01N 1/4044; G01N 1/4055; G01N 30/14;
(Continued)

(56) References Cited

U.S. PATENT DOCUMENTS

2005/0171157 A1    8/2005  Kim et al.

FOREIGN PATENT DOCUMENTS

CA    2507117 A1    11/2006
CN    1563996 A    1/2005
(Continued)

OTHER PUBLICATIONS

Albert et al.; General Approach to Determine Disulfide Connectivity in Cysteine-Rich Peptides by Sequential Alkylation on Solid Phase and Mass Spectrometry; American Chemical Society, 2016, 88, 9539-9546, DOI: 10.1021/acs.analchem.6b02115.
(Continued)

*Primary Examiner* — Jennifer Wecker
*Assistant Examiner* — Michael Paul Shimek
(74) *Attorney, Agent, or Firm* — Novick, Kim & Lee, PLLC; Allen Xue

(57) ABSTRACT

The invention relates to a method for the treatment of body fluid proteins, by which proteins from body fluids such as blood or urine are extracted by adding a certain proportion of high molecular polymer solution under low temperature condition followed by denaturation and reduction by adding a certain concentration of surfactant and tris(2-carboxyethyl) phosphine (TCEP) under a high temperature condition. Subsequently, the iodoacetic acid brushes grafted on silica microspheres called as solid-phase alkylation reagents are added into protein solution, which can react rapidly with the protein sulfhydryl group. After centrifugation, the microspheres are obtained and repeatedly washed with methanol and buffer to remove interferences such as sugars, salts,
(Continued)

Figure 1:
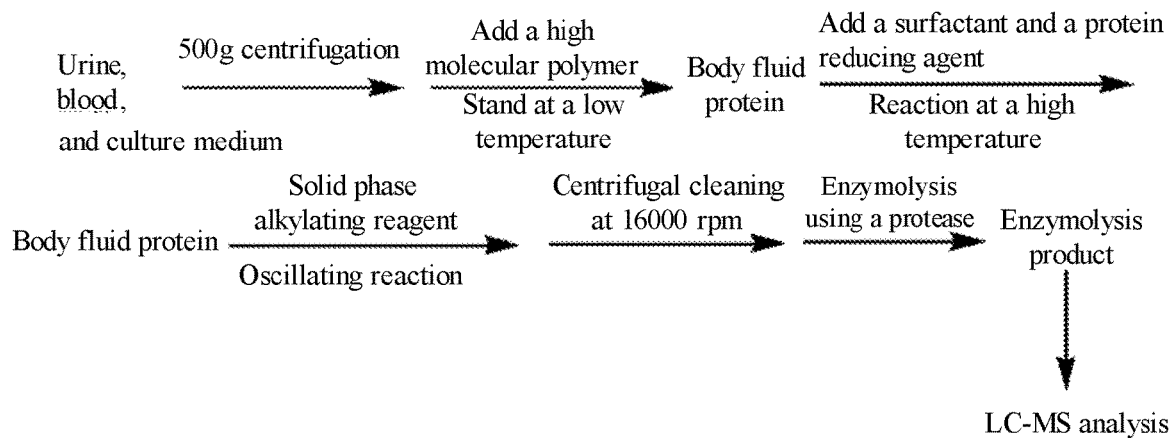

surfactants, lipids to obtain high-purity proteins, and finally protease is added to digest proteins into peptides. After centrifugation, the peptide products are obtained, and directly analyzed by liquid chromatography-mass spectrometry (LC-MS) system. Compared with the traditional protein pretreatment method, the method has many advantages such as good anti-interference capability, easy operation and short pretreatment time.

10 Claims, 2 Drawing Sheets

(51) Int. Cl.
*G01N 1/40* (2006.01)
*G01N 30/14* (2006.01)
*G01N 30/72* (2006.01)
*G01N 30/06* (2006.01)

(52) U.S. Cl.
CPC ........... *G01N 1/4055* (2013.01); *G01N 30/14* (2013.01); *G01N 30/7233* (2013.01); *G01N 2001/4061* (2013.01); *G01N 2030/067* (2013.01)

(58) Field of Classification Search
CPC ....... G01N 30/7233; G01N 2001/4061; G01N 2030/067; G01N 1/34; G01N 30/02
See application file for complete search history.

(56) References Cited

FOREIGN PATENT DOCUMENTS

| | | | |
|---|---|---|---|
| CN | 103172724 A | | 6/2013 |
| CN | 104075931 A | * | 10/2014 |
| CN | 104075931 A | | 10/2014 |
| CN | 104076114 A | | 10/2014 |
| CN | 10578953 A | | 7/2016 |
| CN | 106632877 A | | 5/2017 |

OTHER PUBLICATIONS

Lin et al.; Experiment on Isolating- Human IgG with Polyethylene glycol; The Journal of Fujian Teachers University (Natural Science); 3(1):98-102, 1987.

* cited by examiner

METHOD FOR PRETREATING PROTEIN IN EX VIVO BODY FLUID

FIELD OF TECHNOLOGY

The invention relates to a rapid sample preparation method for exosome proteins, which comprises exosome enrichment, protein extraction, purification and digestion.

BACKGROUND

Body fluids usually carry and transmit important signaling molecules. For example, studies have shown that proteins in urine are mainly derived from glomeruli, renal tubules, prostate, and bladder cells. Therefore, efficient extraction of ultralow-abundance protein in body fluids and then performing the proteome analysis can directly reflect the physiological and pathological state of human tissue organs. However, traditional protein processing methods usually require cumbersome operations, and multi-step sample transfer, which is not only time-consuming and laborious, but also has inevitable sample loss. Furthermore, it is difficult for these methods to achieve efficient treatment of low-abundance proteins. All these problems severely affect the accuracy, sensitivity, and throughput of proteome analysis.

SUMMARY

To solve the above-mentioned problems, the goal of the present invention is to provide an integrated approach, by which the whole sample preparation procedures such as protein extraction, purification and digestion can be completed in the same centrifuge tube, thereby avoiding the loss and pollution caused by the transfer of the sample during the treatment. The method can directly process body fluid proteins without complicated and cumbersome operations. Meanwhile, the entire process maintains a high degree of continuity and high throughput.

To achieve this goal, the technical solution of the present invention is:

1. A certain proportion of high molecular polymer solution is added to body fluid to extract proteins under low temperature conditions. The composition of the high molecular polymer might be polyethylene glycol, polyetherimide and polyvinyl alcohol with a Mr range of 500-10000, or a mixture of more than two polymer, wherein the mass ratio of high molecular polymer accounts for 1%-50% (w/w), the volume ratio of high molecular polymer solution is 1:1-10; The range of temperature is −20-10° C.

2. A certain concentration of surfactant and protein reducing agent are added to rapidly denature the exosome protein under high temperature conditions; wherein the surfactant can be an anionic surfactant (sodium dodecyl alcohol polyoxyethylene ether sulfate, dodecyl benzenesulfonic acid, sodium lauryl sulfate, sodium fatty acid isethionate, ammonium lauryl sulfate or a mixture of more than two anionic surfactants), a cationic surfactant (Octadecyltrimethylammonium chloride, cetyltrimethyl chloride ammonium, distearyl hydroxyethyl methyl sulfate or a mixture of more than two cationic surfactants), a zwitterionic surfactant (Dodecyl betaine, cocoyl imidazoline fatty alcohol, polyoxyethylene ether, sulfosuccinate disodium salt or a mixture of more than two zwitterionic surfactants) and a nonionic surfactant (Coconut fatty acid diethanolamide, nonylphenol polyoxyethylene ether hydroxyl synthetic alcohol, polyoxyethylene ether, C12-14 alkyl glycoside or a mixture of more than two nonionic surfactants), the concentration ranges from 4% to 10% (m/v), the ratio of the surfactant to the obtained solution from step 1 is 1:1-10; protein reducing agent is dithiothreitol or tris(2-carboxyethyl)phosphine or a mixture of them, the final concentration of reducing agent is 10 mM-100 mM; the temperature of protein extraction is 80-95° C.

3. Solid phase alkylating agents capable of rapidly reacting with protein thiol are added to separate proteins from other small molecules to obtain high purity body fluid proteins, wherein the solid phase alkylating agents might be iodoacetic acid-N-succinamide ester modified polymer microspheres or silica microspheres. the mass ratio of protein to solid phase alkylating agent is 1/1-1/5. The matrix of polymer microspheres might be polyacrylate, polystyrene or a mixture of them.

4. Protease is added and incubates with the microspheres that immobilizes proteins at a certain temperature. The proteinase used may be trypsin, lysine protease, protease V8 or a mixture of more than two proteinases; the mass ratio of protein to enzyme is 1/1-1/5, and the enzymatic hydrolysis temperature is 25° C.-37° C., the enzymatic hydrolysis time is 0.5-4 hours.

5. The resulting peptides are analyzed by LC-MS system.

6. The sample preparation method could be applied in rapid processing of exosome proteins in the clinical diagnosis, proteomic research and tumor biomarker screening.

The invention has the following advantages:

1. High molecular weight polymer is used to extract body fluid proteins at low temperature, which improves the extraction efficiency of medium and low abundance proteins in body fluid.

2. The solid phase alkylation reagent is used to covalently bind proteins, which simplifies the steps of purifying proteins, and improves the recovery and pretreatment throughput of body fluid proteins;

3. The protein digests can be directly subjected to liquid chromatography-mass spectrometry to provide technical support for high-throughput clinical proteome analysis.

BRIEF DESCRIPTION THE DRAWINGS

FIG. 1. Schematic diagram of protein pretreatment of body fluid samples.

Figure 2:
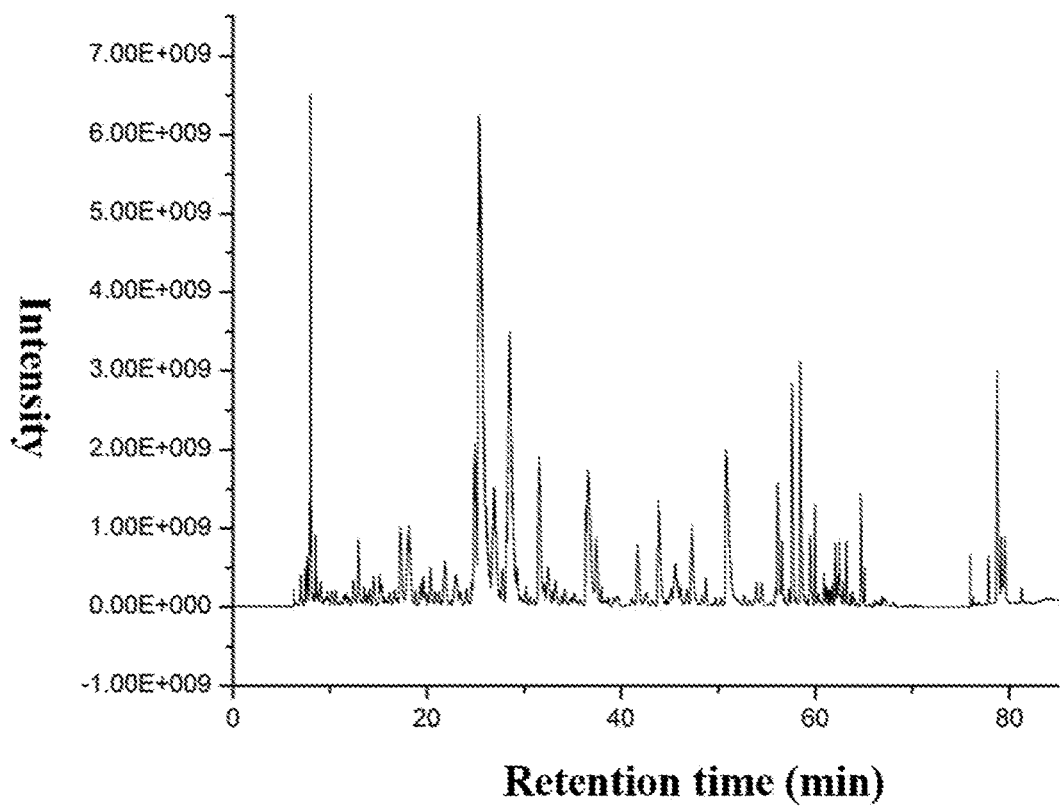

FIG. 2. LC-MS analysis of human urine proteome.

Figure 3:
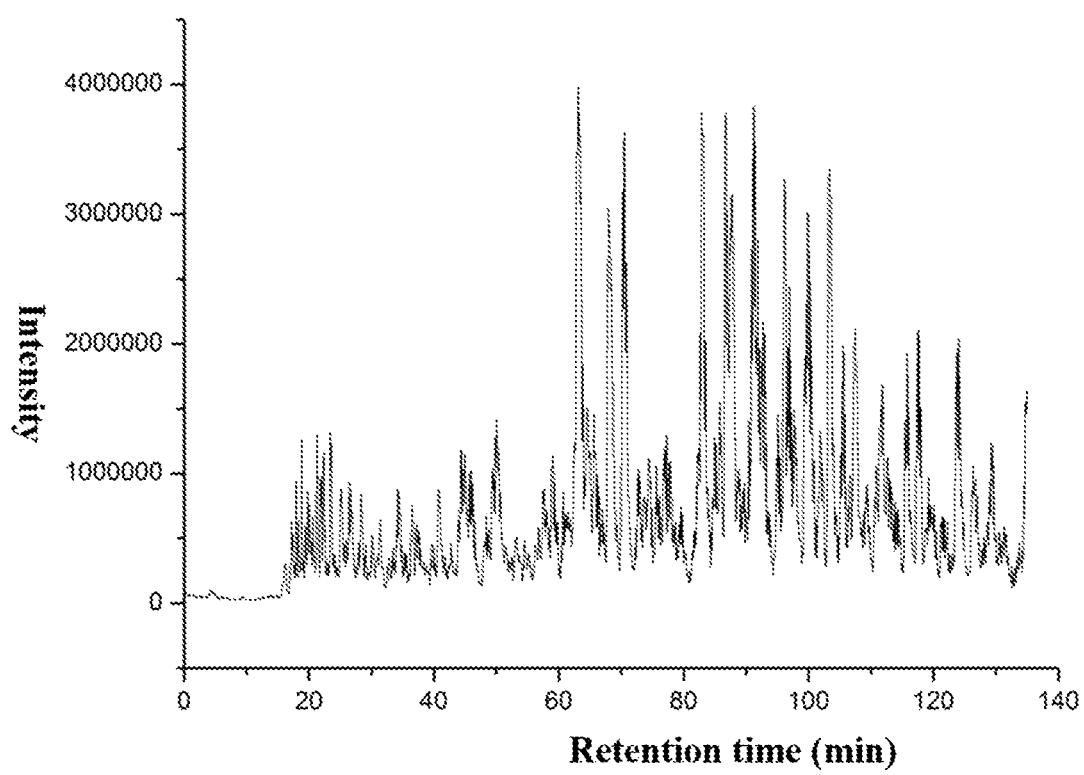

FIG. 3. LC-MS analysis of human plasma proteome.

DETAILED DESCRIPTION OF THE EMBODIMENTS

Embodiment 1

Schematic diagram of body fluid protein pretreatment method is shown in FIG. 1. 10% polyethylene glycol solution was added to 5 mL human urine, and allowed to keep at 0° C. for 1 hour, centrifuged at 16000 rpm for 30 min to obtain exosome in urine, and then 4% SDS and 50 mM tris(2-carboxyethyl)phosphine was added and incubated in a 95° C. water bath for 30 min, subsequently, silica microspheres covalently bonded with iodoacetic acid-N-succinamide ester were added and shaken for 1.5 hours. The supernatant was discarded, and the microspheres were washed by adding 50% methanol and 50 mM ammonium hydrogencarbonate solution respectively. Finally, the trypsin was added with a ratio of proteins to trypsin=1:1 (w/w) and incubated at 37° C. for 30 min, after centrifugation, and the supernatant was obtained, and then subjected to liquid chromatography-mass spectrometry analysis. The results are shown in FIG. 2.

Embodiment 2

A mixture of 10% polyethylene glycol and 20% polyetherimide solution was added to 1 mL human urine, and allowed to keep at 0° C. for 1 hour, centrifuged at 16000 rpm for 30 min to obtain exosome in urine, and then 4% cetyltrimethyl chloride ammonium and 50 mM tris(2-carboxyethyl)phosphine was added and incubated in a 95° C. water bath for 30 min, subsequently, polymer microspheres covalently bonded with iodoacetic acid-N-succinamide ester were added and shaken for 1.5 hours. After centrifugation, the supernatant was discarded, and the microspheres were washed by adding 50% methanol and 50 mM ammonium hydrogencarbonate solution respectively. Finally, the trypsin and Lys-C protease were added with a ratio of proteins to trypsin=1:2 (w/w) and incubated at 37° C. for 1 min, after centrifugation, and the supernatant was obtained, and then subjected to liquid chromatography-mass spectrometry analysis. The results are shown in FIG. 3.

Embodiment 3

A mixture of 50% polyethylene glycol and 20% polyetherimide solution was added to 1 mL human plasma, and allowed to keep at −20° C. for 0.5 hour, centrifuged at 16000 rpm for 30 min to obtain exosome in human plasma, and then 10% fatty alcohol polyoxyethylene ether and 100 mM tris(2-carboxyethyl)phosphine was added and incubated in a 95° C. water bath for 30 min, subsequently, polymer microspheres covalently bonded with iodoacetic acid-N-succinamide ester were added and shaken for 1.5 hours. After centrifugation, the supernatant was discarded, and the microspheres were washed by adding 50% methanol and 50 mM ammonium hydrogencarbonate solution respectively. Finally, the trypsin was added with a ratio of proteins to enzyme=1:3 (w/w) and incubated at 37° C. for 1 min, after centrifugation, and the supernatant was obtained, and then subjected to liquid chromatography-mass spectrometry analysis.

Embodiment 4

A mixture of 50% polyethylene glycol and 20% Polyetherimide solution was added to 50 mL human plasma, and allowed to keep at 0° C. for 0.5 hour, centrifuged at 16000 rpm for 30 min to obtain exosome in urine, and then 10% fatty alcohol polyoxyethylene ether and 100 mM tris(2-carboxyethyl)phosphine was added and incubated in a 95° C. water bath for 30 min, subsequently, polymer microspheres covalently bonded with iodoacetic acid-N-succinamide ester were added and shaken for 1.5 hours. After centrifugation, the supernatant was discarded, and the microspheres were washed by adding 50% methanol and 50 mM ammonium hydrogencarbonate solution respectively. Finally, the trypsin was added with a ratio of proteins to enzyme=1:4 (w/w) and incubated at 37° C. for 1 min, after centrifugation, and the supernatant was obtained, and then subjected to liquid chromatography-mass spectrometry analysis.

Embodiment 5

A mixture of 10% polyethylene glycol, 10% polyvinyl alcohol and 20% polyetherimide solution was added to 50 mL human plasma, and allowed to keep at −5° C. for 0.5 hour, centrifuged at 16000 rpm for 30 min to obtain exosome in urine, and then 10% SDS and 50 mM dithiothreitol was added and incubated in a 80° C. water bath for 30 min, subsequently, silica microspheres covalently bonded with iodoacetic acid-N-succinamide ester were added and shaken for 1.5 hours. After centrifugation, the supernatant was discarded, and the microspheres were washed by adding 50% methanol and 0.1% formic acid solution respectively. Finally, protease V8 was added with a ratio of proteins to enzyme=1:5 (w/w) and incubated at 37° C. for 30 min, after centrifugation, and the supernatant was obtained, and then subjected to liquid chromatography-mass spectrometry analysis.

We claim:

1. A method for treating body fluid proteins, comprising: mixing a solution containing a polymer with a blood sample or a urine sample at a temperature of 10-20° C. to form a mixture;
adding a surfactant and a reducing agent to the mixture at a temperature of 80-95° C. to denature proteins in the mixture; and adding a solid-phase alkylation reagent configured to bind a denatured protein; and contacting a protease with the denatured protein bound to the solid-phase alkylation reagent, wherein the solid-phase alkylating reagent is an iodoacetic acid-N-succinamide ester modified polymer microsphere or silica microsphere.

2. The method according to claim 1, wherein the polymer in the solution has a Mr in a range of 500-10000 and is selected from polyethylene glycol, polyetherimide, polyvinyl alcohol, and mixtures thereof.

3. The method according to claim 1, wherein the surfactant is selected from anionic surfactants, sodium dodecyl alcohol polyoxyethylene ether sulfate, dodecyl benzenesulfonic acid, sodium lauryl sulfate, sodium fatty acid isethionate, ammonium lauryl sulfate, cationic surfactants, octadecyltrimethylammonium chloride, cetyltrimethyl chloride ammonium, distearyl hydroxyethyl methyl sulfate, zwitterionic surfactants, dodecyl betaine, cocoyl imidazoline fatty alcohol, polyoxyethylene ether, sulfosuccinate disodium salt, nonionic surfactants coconut fatty acid diethanolamide, nonylphenol polyoxyethylene ether hydroxyl synthetic alcohol, polyoxyethylene ether, C12-14 alkyl glycoside, and mixtures thereof.

4. The method according to claim 1, wherein a mass ratio of the denatured protein to the solid phase alkylating agent is 1:1 to 1:5, and a matrix of the polymer microsphere is polyacrylate, polystyrene, or a mixture thereof.

5. The method according to claim 1, wherein the protease is selected from trypsin, lysine protease, protease V8, and mixtures thereof.

6. The method according to claim 1, wherein the polymer accounts for 1%-50% (w/w) of the solution.

7. The method according to claim 1, wherein a volume ratio of the polymer solution to a volume of the blood sample or the urine sample is 1:1 to 1:10.

8. The method according to claim 1, wherein a concentration of the surfactant is 4% to 10% (m/v) and a volume ratio of the surfactant and the mixture is 1:1 to 1:10.

9. The method according to claim 1, wherein the reducing agent is dithiothreitol, tris(2-carboxyethyl)phosphine, or a mixture thereof.

10. The method according to claim 1, wherein a mass ratio of the body fluid proteins to the protease is 1:1 to 1:5.

* * * * *